United States Patent
Wen et al.

(10) Patent No.: US 12,403,097 B2
(45) Date of Patent: *Sep. 2, 2025

(54) CONTROLLED-RELEASE TABLET OF IBUPROFEN AND METHOD FOR PREPARING SAME

(71) Applicant: OVERSEAS PHARMACEUTICALS, LTD., Guangzhou (CN)

(72) Inventors: Xiaoguang Wen, Guangzhou (CN); Xiaofeng Huang, Guangzhou (CN); Dachuan Zhao, Guangzhou (CN); Jun Fan, Guangzhou (CN); Chenliang Zhang, Guangzhou (CN); Peipei Wang, Guangzhou (CN); Min Li, Guangzhou (CN)

(73) Assignee: OVERSEAS PHARMACEUTICALS, LTD., Guangzhou (CN)

( * ) Notice: Subject to any disclaimer, the term of this patent is extended or adjusted under 35 U.S.C. 154(b) by 0 days.

This patent is subject to a terminal disclaimer.

(21) Appl. No.: 18/118,790

(22) Filed: Mar. 8, 2023

(65) Prior Publication Data

US 2023/0210779 A1     Jul. 6, 2023

Related U.S. Application Data

(63) Continuation of application No. PCT/CN2021/116700, filed on Sep. 6, 2021.

(30) Foreign Application Priority Data

Sep. 8, 2020 (CN) .......................... 202010934282.8
Aug. 31, 2021 (CN) .......................... 202111009666.X (51) Int. Cl.
A61K 31/192     (2006.01)
A61K 9/20       (2006.01)
A61K 9/24       (2006.01)

(52) U.S. Cl.
CPC ............ *A61K 9/209* (2013.01); *A61K 9/2009* (2013.01); *A61K 9/2013* (2013.01); *A61K 9/2027* (2013.01); *A61K 9/205* (2013.01); *A61K 9/2054* (2013.01); *A61K 9/2095* (2013.01); *A61K 31/192* (2013.01)

(58) Field of Classification Search
None
See application file for complete search history.

(56) References Cited

U.S. PATENT DOCUMENTS 4,806,359 A  *  2/1989  Radebaugh .......... A61K 9/2095
                                              424/472
2017/0319521 A1*  11/2017  Dill ........................ A61K 31/46

FOREIGN PATENT DOCUMENTS

| CN | 202314482 U   | 7/2012 |
| CN | 103655505 A   | 3/2014 |
| CN | 104248767 A   | 12/2014 |
| WO | 2015154655 A1 | 10/2015 |

OTHER PUBLICATIONS

Chen Biao, et al., Research overview of ibuprofen sustained-release formulations, Journal of Pharmaceutical Practice, 2006, pp. 65-69, vol. 24, No. 2.

* cited by examiner

*Primary Examiner* — Frederick F Krass
*Assistant Examiner* — Ashlee E Wertz
(74) *Attorney, Agent, or Firm* — Bayramoglu Law Offices LLC (57) ABSTRACT

An ibuprofen controlled-release tablet and a method for preparing same are provided. The controlled-release tablet is composed of a drug-containing immediate-release layer and a drug-containing sustained-release layer, wherein a mass of ibuprofen in the drug-containing sustained-release layer is greater than a mass of ibuprofen in the drug-containing immediate-release layer, and a ratio of the mass of the ibuprofen in the drug-containing sustained-release layer to the mass of the ibuprofen in the drug-containing immediate-release layer is ≤7. The tablet of the present disclosure has an effective analgesic effect for 24 h after administration.

26 Claims, 4 Drawing Sheets

CONTROLLED-RELEASE TABLET OF IBUPROFEN AND METHOD FOR PREPARING SAME

CROSS REFERENCE TO THE RELATED APPLICATIONS

This application is a continuation application of International Application No. PCT/CN2021/116700, filed on Sep. 6, 2021, which is based upon and claims priority to Chinese Patent Applications No. 202010934282.8, filed on Sep. 8, 2020, and No. 202111009666.X, filed on Aug. 31, 2021, the entire contents of which are incorporated herein by reference.

TECHNICAL FIELD

The present disclosure belongs to the technical field of medicines and in particular, to an ibuprofen controlled-release tablet and a method for preparing same.

BACKGROUND

Ibuprofen has anti-inflammatory, analgesic, and antipyretic effects, and is one of the most widely used anti-inflammatory, analgesic, and antipyretic drugs. In 1969, the ibuprofen was first used to treat rheumatism and pains. The ibuprofen is now used to relieve and treat pains of non-serious arthritis, rheumatism, muscle pains, back pains, neuralgia, headache (including migraine), dental pains, dysmenorrhea, fever, cold, and influenza.

Pain is a huge global problem. It is estimated that about 20% of adults suffer from pain worldwide. Pain can cause a variety of serious problems to human body, including but not limited to depression, inability to work, interruption of social relations, and suicidal thoughts. Therefore, pain can affect normal life of people.

At present, the ibuprofen on the market is divided into two types, an immediate-release type and a sustained-release type. The immediate-release dosage releases rapidly. But since the ibuprofen has a short half-life period ($t_{1/2}$ about 2 h), the drug is quickly eliminated in the body, such that the drug efficacy cannot be sustained and a patient needs to be administered many times. At present, the sustained-release dosage on the market can take effect continuously for a certain period of time, reduce the number of times of administration, and improve compliance of a patient, but the drug cannot take effect quickly after the administration and cannot rapidly reduce pain of the patient.

The present art needs a preparation that can quickly take effect to inhibit pain, has a long duration of efficacy, can be taken once a day, and has an analgesic effect is better than that of the marketed ibuprofen varieties. At the same time, a preparation process of the preparation needs to be stable and controllable, and suitable for commercial production.

SUMMARY

The objectives of the present disclosure are to overcome the shortcomings of the prior art and provide an ibuprofen controlled-release tablet and a method for preparing same. The ibuprofen controlled-release tablet combines advantages of immediate-release and sustained-release dosages. After a patient takes a drug, the drug can take effect quickly and can be effective for a long time, and has a positive clinical application value.

The above objectives of the present disclosure are realized by using the following technical solutions.

On the one hand, the present disclosure provides an ibuprofen controlled-release tablet, wherein the controlled-release tablet is composed of a drug-containing immediate-release layer (that is an immediate-release layer containing ibuprofen, also called an immediate-release layer) and a drug-containing sustained-release layer (that is a sustained-release layer containing ibuprofen, also called a sustained-release layer), and a mass of the ibuprofen in the drug-containing sustained-release layer is greater than a mass of the ibuprofen in the drug-containing immediate-release layer.

A ratio of the mass of the ibuprofen in the drug-containing sustained-release layer to the mass of the ibuprofen in the drug-containing immediate-release layer is ≤7, preferably, a ratio of the mass of the ibuprofen in the drug-containing sustained-release layer to the mass of the ibuprofen in the drug-containing immediate-release layer is 7:1 to 2.2:1, 3:1 to 7:1, 4:1 to 7:1, 2.5 to 7:1, 6:1 to 7:1, 2.2:1 to 3:1, 2.2:1 to 4:1, 2.2:1 to 5:1, 2.2:1 to 6:1, 3:1 to 4:1, 4:1 to 5:1 or 5:1 to 6:1.

Preferably, the drug-containing immediate-release layer is composed of the following components: ibuprofen, a filler, an adhesive, a disintegrating agent, a lubricant, and a flow aid, preferably, calculated by the ibuprofen controlled-release tablet, the drug-containing immediate-release layer contains 5.00-30.00 wt % of the ibuprofen and 0.50-5.00 wt % of the disintegrating agent, preferably, calculated by the ibuprofen controlled-release tablet, the drug-containing immediate-release layer is composed of the following components: 5.00-30.00% of the ibuprofen, 2.50-15.00% of the filler, 1.00-5.00% of the adhesive, 0.50-5.00% of the disintegrating agent, 0.05-0.5% of the lubricant, and 0.05-0.50% of the flow aid.

More preferably, calculated by the ibuprofen controlled-release tablet, the drug-containing immediate-release layer is composed of the following components: 6.02-23.04% of the ibuprofen, 4.70-9.37% of the filler, 1.13-2.76% of the adhesive, 0.64-2.35% of the disintegrating agent, 0.08-0.16% of the lubricant, and 0.15-0.32% of the flow aid.

Preferably, the drug-containing sustained-release layer is composed of the following components: ibuprofen, a sustained-release polymer, a filler, a lubricant, and a flow aid.

Preferably, calculated by the ibuprofen controlled-release tablet, the drug-containing immediate-release layer contains 30.00-65.00 wt % of the ibuprofen and 5.00-25.00 wt % of the sustained-release polymer, preferably, calculated by the ibuprofen controlled-release tablet, the drug-containing sustained-release layer is composed of the following components: 30.00-65.00% of the ibuprofen, 5.00-25.00% of the sustained-release polymer, 1.50-25.00% of the filler, 0.10-0.50% of the lubricant, and 0.10-0.50% of the flow aid.

More preferably, calculated by the ibuprofen controlled-release tablet, the drug-containing sustained-release layer is composed of the following components: 39.16-50.98% of the ibuprofen, 11.44-21.97% of the sustained-release polymer, 2.13-19.82% of the filler, 0.34-0.42% of the lubricant, and 0.16-0.21% of the flow aid.

Preferably, the sustained-release polymer contains xanthan gum and the content of the xanthan gum is 5-10 wt % calculated by the ibuprofen controlled-release tablet.

Preferably, a ratio of the mass of the drug-containing sustained-release layer to the mass of the drug-containing immediate-release layer is 5.6:1 to 1.66:1.

Preferably, the controlled-release tablet is oval or capsule-shaped; The drug-containing immediate-release layer and the drug-containing sustained-release layer separately constitute an upper layer and a lower layer of the ibuprofen controlled-release tablet.

The shape of the ibuprofen controlled-release tablet will affect compliance of a patient, preferably the controlled-release tablet is oval. If a dose is 800 mg, a length and a width of the tablet is preferably 21 mm×10 mm, and a thickness of the tablet is preferably 5-9 mm. A size of the tablet can be adjusted to appropriately according to the dose and tablet weight.

Preferably, during a pressing process of the controlled-release tablet, a pre-pressure range is 0.1-2 KN, preferably 0.1-0.5 KN; and a main pressure range is 5-60 KN, preferably 10-50 KN.

Preferably, the ibuprofen controlled-release tablet further comprises a tablet core layer wrapped between the drug-containing immediate-release layer and the drug-containing sustained-release layer.

Preferably, the tablet core layer is an immediate-release tablet core layer or a sustained-release tablet core layer.

Preferably, when the tablet core layer is the sustained-release tablet core layer, a ratio of a sum of the mass of the ibuprofen in the drug-containing sustained-release layer and the sustained-release tablet core layer to the mass of the ibuprofen in the drug-containing immediate-release layer is 2.2:1 to 7:1, 3:1 to 7:1, 4:1 to 7:1, 2.5 to 7:1, 6:1 to 7:1, 2.2:1 to 3:1, 2.2:1 to 4:1, 2.2:1 to 5:1, 2.2:1 to 6:1, 3:1 to 4:1, 4:1 to 5:1 or 5:1 to 6:1, and a ratio of the mass of the ibuprofen in the drug-containing sustained-release layer to the mass of the ibuprofen in the sustained-release tablet core layer is 27:1 to 3:1 or 19:1 to 4.6:1.

When the tablet core layer is the immediate-release tablet core layer, a ratio of the mass of the ibuprofen in the drug-containing sustained-release layer to a sum of the mass of the ibuprofen in the immediate-release tablet core layer and the drug-containing immediate-release layer is 2.2:1 to 7:1, 3:1 to 7:1, 4:1 to 7:1, 2.5 to 7:1, 6:1 to 7:1, 2.2:1 to 3:1, 2.2:1 to 4:1, 2.2:1 to 5:1, 2.2:1 to 6:1, 3:1 to 4:1, 4:1 to 5:1 or 5:1 to 6:1, and a ratio of the mass of the ibuprofen in the drug-containing immediate-release layer to the mass of the ibuprofen in the immediate-release tablet core layer is 11:1 to 1:1 or 10:1 to 2:1.

Preferably, the tablet core layer is circular with a diameter of ≤7 mm (for example, 6 mm) and a weight of a tablet core accounts for 6.63-13.32% of a total tablet weight.

Preferably, the sustained-release tablet core layer is composed of the following components: the ibuprofen, the sustained-release polymer, the filler, the lubricant, the flow aid, and an enteric coating premix.

Preferably, calculated by the ibuprofen controlled-release tablet, the sustained-release tablet core layer is composed of the following components: 2.00-10.00% of the ibuprofen, 0.50-5.00% of the sustained-release polymer, 0.50-5.00% of the filler, 0.01-2.00% of the lubricant, 0.01-2.00% of the flow aid, and 0.500-5.00% of the enteric coating premix.

More preferably, calculated by the ibuprofen controlled-release tablet, the sustained-release tablet core layer is composed of the following components: 2.50-7.50% of the ibuprofen, 1.00-3.00% of the sustained-release polymer, 1.00-3.00% of the filler, 0.03-1.00% of the lubricant, 0.01-1.00% of the flow aid, and 0.50-3.00% of the enteric coating premix.

Preferably, the immediate-release tablet core layer is composed of the following components: the ibuprofen, the filler, the adhesive, the disintegrating agent, the lubricant, the flow aid, and the enteric coating premix.

Preferably, calculated by the ibuprofen controlled-release tablet, the immediate-release tablet core layer is composed of the following components: 3.00-15.00% of the ibuprofen, 0.30-5.00% of the filler, 0.50-8.00% of the adhesive, 0.20-5.00% of the disintegrating agent, 0.05-2.00% of the lubricant, 0.01-2.00% of the flow aid, and 0.50-5.00% of the enteric coating premix.

More preferably, calculated by the ibuprofen controlled-release tablet, the immediate-release tablet core layer is composed of the following components: 2.00-10.00% of the ibuprofen, 0.50-3.00% of the filler, 0.50-5.00% of the adhesive, 0.20-2.00% of the disintegrating agent, 0.03-1.00% of the lubricant, 0.01-1.00% of the flow aid, and 0.50-3.00% of the enteric coating premix.

Preferably, the filler in the drug-containing immediate-release layer, the drug-containing sustained-release layer, the immediate-release tablet core layer, and the sustained-release tablet core layer is independently selected from one or more of lactose, corn starch, pregelatinized starch, and microcrystalline cellulose, preferably, corn starch, pregelatinized starch or microcrystalline cellulose.

Preferably, the adhesive in the drug-containing immediate-release layer and the immediate-release tablet core layer is independently selected from one or more of sodium carboxymethyl cellulose, polyvinyl pyrrolidone, and hydroxypropylcellulose (HPC), preferably polyvinyl pyrrolidone or hydroxypropylmethylcellulose (HPMC).

Preferably, the disintegrating agent in the drug-containing immediate-release layer and the immediate-release tablet core layer is independently selected from one or more of cross-linked sodium carboxymethyl starch, cross-linked sodium carboxymethyl cellulose, cross-linked polyvinyl pyrrolidone (PVPP), and low-substituted hydroxypropyl cellulose (L-HPC), preferably cross-linked sodium carboxymethyl starch or cross-linked sodium carboxymethyl cellulose.

Preferably, the lubricant in the drug-containing immediate-release layer, the drug-containing sustained-release layer, the immediate-release tablet core layer, and the sustained-release tablet core layer is independently selected from one or more of magnesium stearate, stearic acid, sodium stearyl fumarate, glyceryl behenate, hydrogenated castor oil, and sodium dodecyl sulfate, preferably magnesium stearate or stearic acid.

Preferably, the flow aid in the drug-containing immediate-release layer, the drug-containing sustained-release layer, the immediate-release tablet core layer, and the sustained-release tablet core layer is independently selected from colloidal silicon dioxide or talc powder, preferably colloidal silicon dioxide.

Preferably, the sustained-release polymer in the drug-containing sustained-release layer and the sustained-release tablet core layer is a combination of hydroxypropylmethylcellulose and xanthan gum.

Preferably, the enteric coating premix in the immediate-release tablet core layer and the sustained-release tablet core layer is independently selected from one or more of a methacrylic acid copolymer, polyvinyl acetate phthalate, and Opadry, preferably a methacrylic acid copolymer.

Preferably, the content of the xanthan gum (XG) in the controlled-release tablet is 5.00-10.00%. The content of the substance plays a key role in controlling a drug release. The present disclosure finds that when a ratio of the xanthan gum in a formulation is greater than 10%, the following problems are caused: (1) in a wet granulation, an organic solvent in a granulating solution needs to be increased in an extremely large proportion, otherwise during the wet granulation process, serious blocking of a sieve will be caused, and thus a yield declines sharply and even the process cannot be performed; (2) increasing the proportion of the organic solvent in the granulating solution will increase a cost and risks of the process, and meanwhile, a production device needs to be equipped with a blasting protection facility, which greatly increases the production cost; (3) increasing the proportion of the organic solvent in the granulating solution will also lead to an increase in a residual amount of the organic solvent in a final tablet, which increases an unsafe risk of the tablet; (4) due to a special property of the xanthan gum, when the proportion of the xanthan gum in the formulation is more than 10%, particle compressibility will be reduced, a hardness of the tablet cannot be improved to meet a normal hardness requirement, and thus fragility of the tablet is non-conformity and the tablet is cracked; (5) when the proportion of the xanthan gum in the formulation is greater than 10%, a dissolution rate in vitro will increase significantly after an accelerated stability test of the tablet for a period of time (see FIG. 9); and (6) when the formulation proportion of the xanthan gum is greater than 10% or even higher, a sticking problem of ibuprofen during pressing is more serious. Therefore, the present application can avoid all the above problems by adjusting the formulation and reducing the proportion of the xanthan gum to 5.00-10.00%. Besides, the tablet can also be continuously effective in vivo for 24 h.

Preferably, calculated by the ibuprofen controlled-release tablet, the content of the hydroxypropylmethylcellulose (HPMC) in the sustained-release polymer is 1-25%, preferably 1.58-16.97%.

Preferably, the hydroxypropylmethylcellulose (HPMC) in the sustained-release polymer has a viscosity range of 3-2,000 mpa·s.

Preferably, the hydroxypropylmethylcellulose (HPMC) in the sustained-release polymer of the controlled-release tablet is selected from one or more of E3LV, E5LV, E6LV, E15LV, E30LV, E50LV, K100LV, SH50, SH400, and SH1500.

In the ibuprofen controlled-release tablet, the hydroxypropylmethylcellulose (HPMC) in the sustained-release polymer plays an important role in controlling a drug release. An optimal formulation proportion of the HPMC in the sustained-release polymer is 1.58%-16.97%. The viscosity of the HPMC has an important effect on drug dissolution. The optimal viscosity range is 3-2,000 mpa·s. In the present application, the HPMC is selected from one or more of E3LV, E5LV, E6LV, E15LV, E30LV, E50LV, K100LV, SH50, SH400, and SH1500.

The weight of the ibuprofen controlled-release tablet increases with an increase of a dose. If the dose is 800 mg, a tablet weight range of the sustained-release layer is 625 mg-1,400 mg and a tablet weight range of the immediate-release layer is 250 mg-375 mg. If the dose is 800 mg, in a human body PK experiment under fasting, a plasma concentration can reach 5.0 μg/mL within 1 h-24 h.

On the other hand, the present disclosure provides a method for preparing an ibuprofen controlled-release tablet, comprising the following steps:
  a. weighing a formulation amount of the ibuprofen and the filler required to prepare the drug-containing immediate-release layer, performing wet granulation by using purified water or an alcohol solution, passing a wet particle through a 1,000-8,000 μm sieve, drying the particle, passing the dried particle through a 1,000-8,000 μm sieve, adding the adhesive, the disintegrating agent, and the flow aid, pre-mixing same, and then adding the lubricant to be mixed to prepare a drug-containing immediate-release layer particle for later use;
  b. weighing a formulation amount of the ibuprofen, the sustained-release polymer, and the filler required to prepare the drug-containing sustained-release layer, performing wet granulation by using purified water or an alcohol solution, passing a wet particle through a 1,000-8,000 μm sieve, drying the particle, passing the dried particle through a 1,000-8,000 μm sieve, adding the flow aid, pre-mixing same, and then adding the lubricant to be mixed to prepare a drug-containing sustained-release layer particle for later use;
  d. placing a formulation amount of the drug-containing sustained-release layer particle into a punching die of a tablet machine for pre-pressing; and then placing a formulation amount of the drug-containing immediate-release layer particle into the punching die to be pressed into a tablet.

Preferably, the present disclosure provides a method for preparing an ibuprofen controlled-release tablet, comprising the following steps:
  a. weighing a formulation amount of the ibuprofen and the filler required to prepare the drug-containing immediate-release layer, performing wet granulation by using purified water or an alcohol solution, passing a wet particle through a 1,000-8,000 μm sieve, drying the particle, passing the dried particle through a 1,000-8,000 μm sieve, adding the adhesive, the disintegrating agent, and the flow aid, pre-mixing same, and then adding the lubricant to be mixed to prepare a drug-containing immediate-release layer particle for later use;
  b. weighing a formulation amount of the ibuprofen, the sustained-release polymer, and the filler required to prepare the drug-containing sustained-release layer, performing wet granulation by using purified water or an alcohol solution, passing a wet particle through a 1,000-8,000 μm sieve, drying the particle, passing the dried particle through a 1,000-8,000 μm sieve, adding the flow aid, pre-mixing same, and then adding the lubricant to be mixed to prepare a drug-containing sustained-release layer particle for later use;
  c. placing the prepared drug-containing immediate-release layer or the drug-containing sustained-release layer particles into a punching die of a tablet machine to be pressed into a plain tablet core;
  e. weighing a formulation amount of the enteric coating premix and preparing same into an enteric coating solution by using an alcohol solution; and placing the plain tablet core pressed in step c in a coating machine and performing coating by using the prepared enteric coating solution to prepare a tablet core layer for later use; and
  f. placing a formulation amount of the sustained-release layer particle into the punching die of the tablet machine, placing the tablet core layer on the sustained-release layer for pre-pressing; and then placing a formulation amount of the immediate-release layer particle into the punching die to be pressed into a tablet.

Preferably, in step d or f, a pre-pressure is 0.1-2 KN, preferably 0.1-0.5 KN; and a main pressure is 5-60 KN, preferably 10-50 KN. During the pressing process of the ibuprofen controlled-release tablet, the pre-pressure has an important effect on hardness and fragility of the tablet. Too small pre-pressure leads to an insufficient filling amount and thus a target tablet weight cannot be reached. Too large pre-pressure leads to cracking of the tablet. An optimal range of the pre-pressure is 0.1-0.5 KN. The main pressure will also affect the hardness and fragility of the tablet. Too small main pressure may lead to a failure to reach a target hardness and a non-conformity fragility. Too large pre-pressure may lead to cracking or hardness exceeding a limit. An optimal range of the main pressure is 10-50 KN.

The ibuprofen controlled-release tablet provided by the present disclosure takes effects rapidly and continuously. A preparation process is easy to control and easy for an expanded production, and does not produce impurities in the process. The prepared ibuprofen controlled-release tablet has a stable structure to ensure a predetermined drug release model. In the preferred embodiment, the present disclosure has the following technical effects: taking a 800-mg tablet as an example, under a dissolution condition of a test of the present disclosure, a dissolution rate in vitro is 20%-40% for 1 h and >90% for 18 h. Under a fasting condition, after 1 tablet of the drug is taken, the drug-containing immediate-release layer rapidly disintegrates to release a drug, the ibuprofen rapidly takes effect to inhibit pain, and meanwhile, the drug-containing sustained-release layer can slowly control the drug release, and a plasma concentration in vivo can reach 5.0 μg/mL within 1-24 h. That is after 1 ibuprofen tablet provided by the present disclosure is taken, an effective analgesic effect for 24 h can be reached.

DETAILED DESCRIPTION OF THE EMBODIMENTS

The present disclosure will be further described below in detail via examples.

A dissolution condition used in the following examples are as follows: a paddle method+settling basket, 900 mL of a dissolution medium of a phosphate buffer solution at a pH of 7.2+2% SDS, a rotation speed of 200 rpm, and a solution temperature of 37° C.

Example 1 Preparation of 1,000 Ibuprofen Controlled-Release Tablets (not Containing Tablet Core)

Taking a preparation of 1,000 ibuprofen controlled-release tablets as an example, each component and dose are shown in the following table:

| Tablet layer | Formulation | Mass (g) |
| --- | --- | --- |
| Immediate-release layer | Ibuprofen | 100.00 |
| | Pregelatinized starch | 96.20 |
| | Cross-linked sodium carboxymethyl starch | 31.20 |
| | Sodium carboxymethyl cellulose | 18.81 |
| | Talc powder | 2.50 |
| | Stearic acid | 1.32 |
| Sustained-release layer | Ibuprofen | 700.00 |
| | Xanthan gum | 82.50 |
| | Hydroxypropylmethylcellulose | 280.01 |
| | Microcrystalline cellulose | 327.03 |
| | Colloidal silicon dioxide | 3.50 |
| | Stearic acid | 6.93 |

A method for preparing an ibuprofen controlled-release tablet in example 1 of the present disclosure comprised the following steps:

a. a formulation amount of 100.00 g of ibuprofen and 96.20 g of a filler required to prepare an immediate-release layer were weighed, wet granulation was performed by using purified water or an alcohol solution, a wet particle was passed through a 1,000-8,000 μm sieve and dried, the dried particle was passed through a 1,000-8,000 μm sieve, 18.81 g of an adhesive, 31.20 g of a disintegrating agent, and 2.50 g of a flow aid were added, the materials were pre-mixed, and then 1.32 g of a lubricant was added to be mixed to prepare an immediate-release layer particle for later use;

b. a formulation amount of 700.00 g of the ibuprofen, 362.51 g of a sustained-release polymer, and 327.03 g of the filler required to prepare a sustained-release layer were weighed, wet granulation was performed by using purified water or an alcohol solution, a wet particle was passed through a 1,000-8,000 μm sieve and dried, the dried particle was passed through a 1,000-8,000 μm sieve, 3.50 g of the flow aid was added, the materials were pre-mixed, and then 6.93 g of the lubricant was added to be mixed to prepare a sustained-release layer particle for later use; and c. a formulation amount of the sustained-release layer particle was placed into a punching die of a tablet machine for pre-pressing at 0.5 KN; and then a formulation amount of the immediate-release layer particle was placed into the punching die to be pressed into a tablet at a main pressure of 10 KN.

Example 2 Preparation of 2,000 Ibuprofen Controlled-Release Tablets (not Containing Tablet Core)

Taking a preparation of 2,000 ibuprofen controlled-release tablets as an example, each component and dose are shown in the following table:

| Tablet layer | Formulation | Mass (g) |
| --- | --- | --- |
| Immediate-release layer | Ibuprofen | 300.00 |
| | Pregelatinized starch | 114.50 |
| | Microcrystalline cellulose | 71.40 |
| | Cross-linked sodium carboxymethyl cellulose | 60.00 |
| | Polyvinyl pyrrolidone K30 | 44.88 |
| | Colloidal silicon dioxide | 6.12 |
| | Magnesium stearate | 3.05 |
| Sustained-release layer | Ibuprofen | 1300.00 |
| | Xanthan gum | 178.50 |
| | Hydroxypropylmethylcellulose | 292.50 |

| Tablet layer | Formulation | Mass (g) |
|---|---|---|
| | Microcrystalline cellulose | 164.50 |
| | Colloidal silicon dioxide | 4.85 |
| | Magnesium stearate | 9.70 |

A method for preparing an ibuprofen controlled-release tablet in example 2 of the present disclosure comprised the following steps:

a. a formulation amount of 300.00 g of ibuprofen and 185.90 g of a filler required to prepare an immediate-release layer were weighed, wet granulation was performed by using purified water or an alcohol solution, a wet particle was passed through a 1,000-8,000 μm sieve and dried, the dried particle was passed through a 1,000-8,000 μm sieve, 44.88 g of an adhesive, 60.00 g of a disintegrating agent, and 6.12 g of a flow aid were added, the materials were pre-mixed, and then 3.05 g of a lubricant was added to be mixed to prepare an immediate-release layer particle for later use;

b. a formulation amount of 1300.00 g of the ibuprofen, 471.00 g of a sustained-release polymer, and 164.50 g of the filler required to prepare a sustained-release layer were weighed, wet granulation was performed by using purified water or an alcohol solution, a wet particle was passed through a 1,000-8,000 μm sieve and dried, the dried particle was passed through a 1,000-8,000 μm sieve, 4.85 g of the flow aid was added, the materials were pre-mixed, and then 9.70 g of the lubricant was added to be mixed to prepare a sustained-release layer particle for later use; and c. a formulation amount of the sustained-release layer particle was placed into a punching die of a tablet machine for pre-pressing at 0.4 KN; and then a formulation amount of the immediate-release layer particle was placed into the punching die to be pressed into a tablet at a main pressure of 20 KN.

Example 3 Preparation of 800 Ibuprofen Controlled-Release Tablets (not Containing Tablet Core)

Taking a preparation of 800 ibuprofen controlled-release tablets as an example, each component and dose are shown in the following table:

| Tablet layer | Formulation | Mass (g) |
|---|---|---|
| Immediate-release layer | Ibuprofen | 160.00 |
| | Microcrystalline cellulose | 22.00 |
| | Corn starch | 35.10 |
| | Cross-linked polyvinyl pyrrolidone | 19.50 |
| | HPMC E4 | 19.50 |
| | Colloidal silicon dioxide | 2.60 |
| | Sodium stearyl fumarate | 1.30 |
| Sustained-release layer | Ibuprofen | 480.00 |
| | Xanthan gum | 75.50 |
| | Hydroxypropylmethylcellulose | 68.40 |
| | Microcrystalline cellulose | 55.00 |
| | Colloidal silicon dioxide | 1.70 |
| | Hydrogenated castor oil | 3.40 |

A method for preparing an ibuprofen controlled-release tablet in example 3 of the present disclosure comprised the following steps:

a. a formulation amount of 160.00 g of ibuprofen and 57.10 g of a filler required to prepare an immediate-release layer were weighed, wet granulation was performed by using purified water or an alcohol solution, a wet particle was passed through a 1,000-8,000 μm sieve and dried, the dried particle was passed through a 1,000-8,000 μm sieve, 19.50 g of an adhesive, 19.50 g of a disintegrating agent, and 2.60 g of a flow aid were added, the materials were pre-mixed, and then 1.30 g of a lubricant was added to be mixed to prepare an immediate-release layer particle for later use;

b. a formulation amount of 480.00 g of the ibuprofen, 143.90 g of a sustained-release polymer, and 55.00 g of the filler required to prepare a sustained-release layer were weighed, wet granulation was performed by using purified water or an alcohol solution, a wet particle was passed through a 1,000-8,000 μm sieve and dried, the dried particle was passed through a 1,000-8,000 μm sieve, 1.70 g of the flow aid was added, the materials were pre-mixed, and then 3.40 g of the lubricant was added to be mixed to prepare a sustained-release layer particle for later use; and c. a formulation amount of the sustained-release layer particle was placed into a punching die of a tablet machine for pre-pressing at 0.4 KN; and then a formulation amount of the immediate-release layer particle was placed into the punching die to be pressed into a tablet at a main pressure of 20 KN.

Example 4 Preparation of 1,000 Ibuprofen Controlled-Release Tablets (not Containing Tablet Core)

Taking a preparation of 1,000 ibuprofen controlled-release tablets as an example, each component and dose are shown in the following table:

| Tablet layer | Formulation | Mass (g) |
|---|---|---|
| Immediate-release layer | Ibuprofen | 250.00 |
| | Lactose | 51.00 |
| | Low-substituted hydroxypropyl cellulose | 17.50 |
| | Hydroxypropylmethylcellulose E5 | 26.26 |
| | Colloidal silicon dioxide | 3.50 |
| | Glyceryl behenate | 1.74 |
| Sustained-release layer | Ibuprofen | 550.00 |
| | Xanthan gum | 108.50 |
| | Hydroxypropylmethylcellulose | 17.14 |
| | Microcrystalline cellulose | 53.82 |
| | Colloidal silicon dioxide | 1.84 |
| | Magnesium stearate | 3.70 |

A method for preparing an ibuprofen controlled-release tablet in example 4 of the present disclosure comprised the following steps:

a. a formulation amount of 250.00 g of ibuprofen and 51.00 g of a filler required to prepare an immediate-release layer were weighed, wet granulation was performed by using purified water or an alcohol solution, a wet particle was passed through a 1,000-8,000 μm sieve and dried, the dried particle was passed through a 1,000-8,000 μm sieve, 26.26 g of an adhesive, 17.50 g of a disintegrating agent, and 3.50 g of a flow aid were added, the materials were pre-mixed, and then 1.74 g of a lubricant was added to be mixed to prepare an immediate-release layer particle for later use;

b. a formulation amount of 550.00 g of the ibuprofen, 125.64 g of a sustained-release polymer, and 53.82 g of the filler required to prepare a sustained-release layer were weighed, wet granulation was performed by using purified water or an alcohol solution, a wet particle was passed through a 1,000-8,000 μm sieve and dried, the dried particle was passed through a 1,000-8,000 μm sieve, 1.84 g of the flow aid was added, the materials were pre-mixed, and then 3.70 g of the lubricant was added to be mixed to prepare a sustained-release layer particle for later use; and c. a formulation amount of the sustained-release layer particle was placed into a punching die of a tablet machine for pre-pressing at 0.4 KN; and then a formulation amount of the immediate-release layer particle was placed into the punching die to be pressed into a tablet at a main pressure of 20 KN.

Example 5 Preparation of 500 Ibuprofen Controlled-Release Tablets (not Containing Tablet Core)

Taking a preparation of 500 ibuprofen controlled-release tablets as an example, each component and dose are shown in the following table:

| Tablet layer | Formulation | Mass (g) |
| --- | --- | --- |
| Immediate-release layer | Ibuprofen | 150.00 |
| | Microcrystalline cellulose | 15.96 |
| | Cross-linked sodium carboxymethyl cellulose | 4.69 |
| | Hydroxypropyl cellulose | 14.07 |
| | Talc powder | 1.89 |
| | Sodium dodecyl sulfate | 0.90 |
| Sustained-release layer | Ibuprofen | 250.00 |
| | Xanthan gum | 56.10 |
| | Hydroxypropylmethylcellulose | 5.10 |
| | Microcrystalline cellulose | 8.87 |
| | Colloidal silicon dioxide | 0.80 |
| | Magnesium stearate | 1.62 |

A method for preparing an ibuprofen controlled-release tablet in example 5 of the present disclosure comprised the following steps:

a. a formulation amount of 150.00 g of ibuprofen and 15.96 g of a filler required to prepare an immediate-release layer were weighed, wet granulation was performed by using purified water or an alcohol solution, a wet particle was passed through a 1,000-8,000 μm sieve and dried, the dried particle was passed through a 1,000-8,000 μm sieve, 14.07 g of an adhesive, 4.69 g of a disintegrating agent, and 1.89 g of a flow aid were added, the materials were pre-mixed, and then 0.90 g of a lubricant was added to be mixed to prepare an immediate-release layer particle for later use;

b. a formulation amount of 250.00 g of the ibuprofen, 61.20 g of a sustained-release polymer, and 8.87 g of the filler required to prepare a sustained-release layer were weighed, wet granulation was performed by using purified water or an alcohol solution, a wet particle was passed through a 1,000-8,000 μm sieve and dried, the dried particle was passed through a 1,000-8,000 μm sieve, 0.80 g of the flow aid was added, the materials were pre-mixed, and then 1.62 g of the lubricant was added to be mixed to prepare a sustained-release layer particle for later use; and c. a formulation amount of the sustained-release layer particle was placed into a punching die of a tablet machine for pre-pressing at 0.4 KN; and then a formulation amount of the immediate-release layer particle was placed into the punching die to be pressed into a tablet at a main pressure of 20 KN.

Example 6 Preparation of 500 Ibuprofen Controlled-Release Tablets (not Containing Tablet Core)

Taking a preparation of 500 ibuprofen controlled-release tablets as an example, each component and dose are shown in the following table:

| Tablet layer | Formulation | Mass (g) |
| --- | --- | --- |
| Immediate-release layer | Ibuprofen | 75.00 |
| | Pregelatinized starch | 28.62 |
| | Microcrystalline cellulose | 17.85 |
| | Cross-linked sodium carboxymethyl cellulose | 14.98 |
| | Polyvinyl pyrrolidone K30 | 11.22 |
| | Colloidal silicon dioxide | 1.54 |
| | Magnesium stearate | 0.78 |
| Sustained-release layer | Ibuprofen | 325.00 |
| | Xanthan gum | 76.50 |
| | Hydroxypropylmethylcellulose | 73.13 |
| | Microcrystalline cellulose | 9.24 |
| | Colloidal silicon dioxide | 1.22 |
| | Magnesium stearate | 2.42 |

A method for preparing an ibuprofen controlled-release tablet in example 6 of the present disclosure comprised the following steps:

a. a formulation amount of 75.00 g of ibuprofen and 46.47 g of a filler required to prepare an immediate-release layer were weighed, wet granulation was performed by using purified water or an alcohol solution, a wet particle was passed through a 1,000-8,000 μm sieve and dried, the dried particle was passed through a 1,000-8,000 μm sieve, 11.22 g of an adhesive, 14.98 g of a disintegrating agent, and 1.54 g of a flow aid were added, the materials were pre-mixed, and then 0.78 g of a lubricant was added to be mixed to prepare an immediate-release layer particle for later use;

b. a formulation amount of 325.00 g of the ibuprofen, 149.63 g of a sustained-release polymer, and 9.27 g of the filler required to prepare a sustained-release layer were weighed, wet granulation was performed by using purified water or an alcohol solution, a wet particle was passed through a 1,000-8,000 μm sieve and dried, the dried particle was passed through a 1,000-8,000 μm sieve, 1.22 g of the flow aid was added, the materials were pre-mixed, and then 2.42 g of the lubricant was added to be mixed to prepare a sustained-release layer particle for later use; and c. a formulation amount of the sustained-release layer particle was placed into a punching die of a tablet machine for pre-pressing at 0.4 KN; and then a formulation amount of the immediate-release layer particle was placed into the punching die to be pressed into a tablet at a main pressure of 20 KN.

Figure 1:
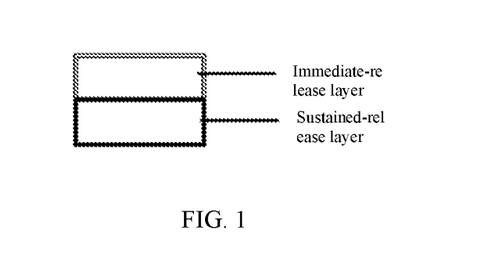
FIG. 1 is a structural diagram of the ibuprofen controlled-release tablet of the present application (not containing a tablet core)
Figure 3:
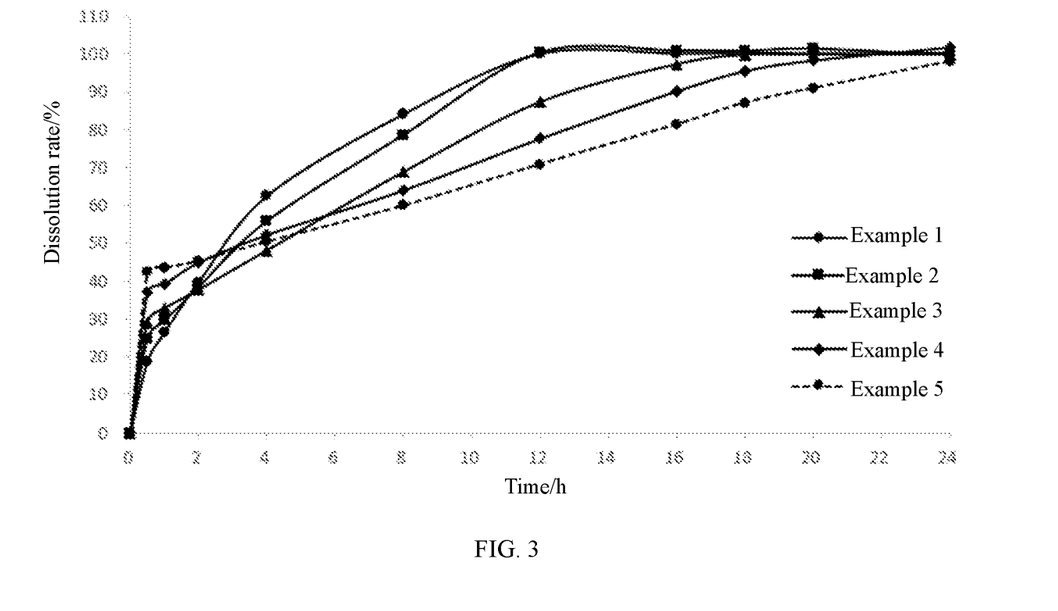
FIG. 3 shows in-vitro dissolution curves of the ibuprofen controlled-release tablets in examples 1-5.
Figure 6:
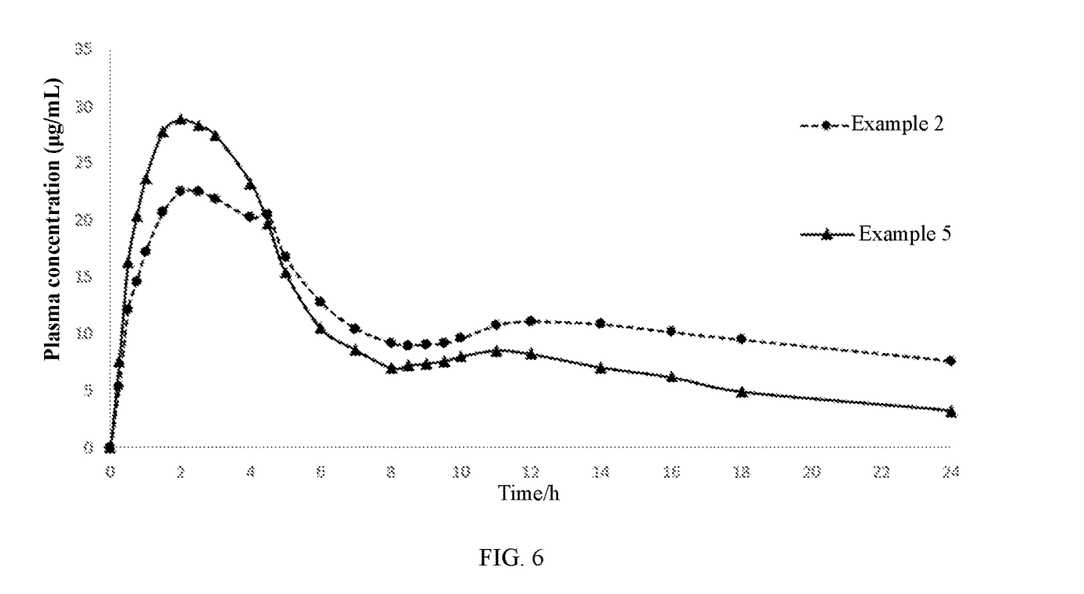
FIG. 6 shows in-vivo curves of the ibuprofen controlled-release tablets in examples 2 and 5.

A structure diagram of the tablets in examples 1-5 are shown in FIG. 1. An in-vitro release of the ibuprofen controlled-release tablets in examples 1-5 and a fasting plasma concentration of the ibuprofen controlled-release tablets in examples 2 and 5 were detected by the aforementioned dissolution method. The results are shown in FIG. 3 and FIG. 6 respectively.

The plasma concentrations of the tablets of examples 1~4 can all reach 5.0 μg/mL within 1-24 h, all higher than 4.0

µg/mL. The plasma concentration of the tablet of example 5 at 24 h is only 3.25 µg/mL, and thus a 24 h long-term analgesic effect cannot be achieved.

Example 7 Preparation of 1,000 Ibuprofen Controlled-Release Tablets (Containing Tablet Core)

Taking a preparation of 1,000 ibuprofen controlled-release tablets as an example, each component and dose are shown in the following table:

| Tablet layer | Formulation | Mass (g) |
|---|---|---|
| Immediate-release layer | Ibuprofen | 100.00 |
| | Corn starch | 59.12 |
| | Microcrystalline cellulose | 37.02 |
| | Cross-linked sodium carboxymethyl starch | 31.25 |
| | Sodium carboxymethyl cellulose | 18.76 |
| | Colloidal silicon dioxide | 2.50 |
| | Magnesium stearate | 1.33 |
| Sustained-release tablet core layer | Ibuprofen | 50.00 |
| | Xanthan gum | 5.98 |
| | Hydroxypropylmethylcellulose | 19.92 |
| | Microcrystalline cellulose | 23.45 |
| | Colloidal silicon dioxide | 0.20 |
| | Magnesium stearate | 0.50 |
| | Enteric coating premix | 9.96 |
| Sustained-release layer | Ibuprofen | 650.00 |
| | Xanthan gum | 76.70 |
| | Hydroxypropylmethylcellulose | 260.00 |
| | Microcrystalline cellulose | 303.65 |
| | Colloidal silicon dioxide | 3.16 |
| | Magnesium stearate | 6.50 |

A method for preparing an ibuprofen controlled-release tablet in example 7 of the present disclosure comprised the following steps:
  a. a formulation amount of 100.00 g of ibuprofen and 96.14 g of a filler required to prepare an immediate-release layer were weighed, wet granulation was performed by using purified water or an alcohol solution, a wet particle was passed through a 1,000-8,000 µm sieve and dried, the dried particle was passed through a 1,000-8,000 µm sieve, 18.76 g of an adhesive, 31.25 g of a disintegrating agent, and 2.50 g of a flow aid were added, the materials were pre-mixed, and then 1.33 g of a lubricant was added to be mixed to prepare an immediate-release layer particle for later use;
  b. a formulation amount of 50.00 g of the ibuprofen, 25.90 g of a sustained-release polymer, and 23.45 g of the filler required to prepare a sustained-release tablet core layer were weighed, wet granulation was performed by using purified water or an alcohol solution, a wet particle was passed through a 1,000-8,000 µm sieve and dried, the dried particle was passed through a 1,000-8,000 µm sieve, 0.20 g of the flow aid was added, the materials were pre-mixed, and then 0.50 g of the lubricant was added to be mixed to prepare a sustained-release layer particle for later use;
  c. a formulation amount of 650.00 g of the ibuprofen, 336.70 g of a sustained-release polymer, and 303.65 g of the filler required to prepare a sustained-release layer were weighed, wet granulation was performed by using purified water or an alcohol solution, a wet particle was passed through a 1,000-8,000 µm sieve and dried, the dried particle was passed through a 1,000-8,000 µm sieve, 3.16 g of the flow aid was added, the materials were pre-mixed, and then 6.50 g of the lubricant was added to be mixed to prepare a sustained-release layer particle for later use;
  d. the prepared sustained-release tablet core layer particle was placed into a punching die of a tablet machine to be pressed into a plain tablet core;
  e. a formulation amount of 9.96 g of the enteric coating premix was weighed and prepared into an enteric coating solution with a solid content of 9.9% by using a 95% alcohol solution; and the plain tablet core pressed in step d was placed in a coating machine to be coated with the prepared enteric coating solution to prepare a tablet core layer for later use; and
  f. a formulation amount of the sustained-release layer particle was placed into the punching die of the tablet machine and the tablet core layer was placed on the sustained-release layer for pre-pressing at 0.5 KN; and then a formulation amount of the immediate-release layer particle was placed into the punching die to be pressed into a tablet at a main pressure of 10 KN.

Example 8 Preparation of 800 Ibuprofen Controlled-Release Tablets (Containing Tablet Core)

Taking a preparation of 800 ibuprofen controlled-release tablets as an example, each component and dose are shown in the following table:

| Tablet layer | Formulation | Mass (g) |
|---|---|---|
| Immediate-release layer | Ibuprofen | 120.00 |
| | Microcrystalline cellulose | 85.32 |
| | Cross-linked sodium carboxymethyl starch | 5.82 |
| | Polyvinyl pyrrolidone K30 | 17.28 |
| | Colloidal silicon dioxide | 2.36 |
| | Magnesium stearate | 1.18 |
| Immediate-release tablet core layer | Ibuprofen | 80.00 |
| | Microcrystalline cellulose | 8.46 |
| | Cross-linked sodium carboxymethyl starch | 2.46 |
| | Polyvinyl pyrrolidone K30 | 7.55 |
| | Magnesium stearate | 1.00 |
| | Magnesium stearate | 0.45 |
| | Enteric coating premix | 9.64 |
| Sustained-release layer | Ibuprofen | 440.00 |
| | Xanthan gum | 89.87 |
| | Hydroxypropylmethylcellulose | 14.20 |
| | Microcrystalline cellulose | 19.37 |
| | Colloidal silicon dioxide | 1.46 |
| | Magnesium stearate | 3.18 |

A method for preparing ibuprofen controlled-release tablets in example 8 of the present disclosure comprised the following steps:
  a. a formulation amount of 120.00 g of ibuprofen and 85.32 g of a filler required to prepare an immediate-release layer were weighed, wet granulation was performed by using purified water or an alcohol solution, a wet particle was passed through a 1,000-8,000 µm sieve and dried, the dried particle was passed through a 1,000-8,000 µm sieve, 17.28 g of an adhesive, 5.82 g of a disintegrating agent, and 2.36 g of a flow aid were added, the materials were pre-mixed, and then 1.18 g of a lubricant was added to be mixed to prepare an immediate-release layer particle for later use;

b. a formulation amount of 80.00 g of ibuprofen and 8.46 g of a filler required to prepare an immediate-release tablet core layer were weighed, wet granulation was performed by using purified water or an alcohol solution, a wet particle was passed through a 1,000-8,000 µm sieve and dried, the dried particle was passed through a 1,000-8,000 µm sieve, 7.55 g of an adhesive, 2.46 g of a disintegrating agent, and 1.00 g of a flow aid were added, the materials were pre-mixed, and then 0.45 g of a lubricant was added to be mixed to prepare an immediate-release tablet core layer particle for later use;

c. a formulation amount of 440.00 g of the ibuprofen, 104.07 g of a sustained-release polymer, and 19.37 g of the filler required to prepare a sustained-release layer were weighed, wet granulation was performed by using purified water or an alcohol solution, a wet particle was passed through a 1,000-8,000 µm sieve and dried, the dried particle was passed through a 1,000-8,000 µm sieve, 1.46 g of the flow aid was added, the materials were pre-mixed, and then 3.18 g of the lubricant was added to be mixed to prepare a sustained-release layer particle for later use;

d. the prepared immediate-release tablet core layer particle was placed into a punching die of a tablet machine to be pressed into a plain tablet core;

e. a formulation amount of 9.64 g of the enteric coating premix was weighed and prepared into an enteric coating solution with a solid content of 9.9% by using a 95% alcohol solution; and the plain tablet core pressed in step d was placed in a coating machine to be coated with the prepared enteric coating solution to prepare a tablet core layer for later use; and f. a formulation amount of the sustained-release layer particle was placed into the punching die of the tablet machine and the tablet core layer was placed on the sustained-release layer for pre-pressing at 0.1 KN; and then a formulation amount of the immediate-release layer particle was placed into the punching die to be pressed into a tablet at a main pressure of 50 KN.

Figure 2:
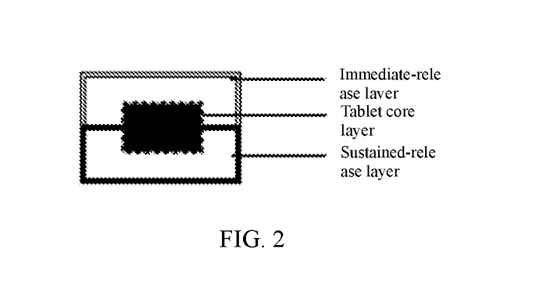
FIG. 2 is a structural diagram of the ibuprofen controlled-release tablet of the present application (containing a tablet core)
Figure 4:
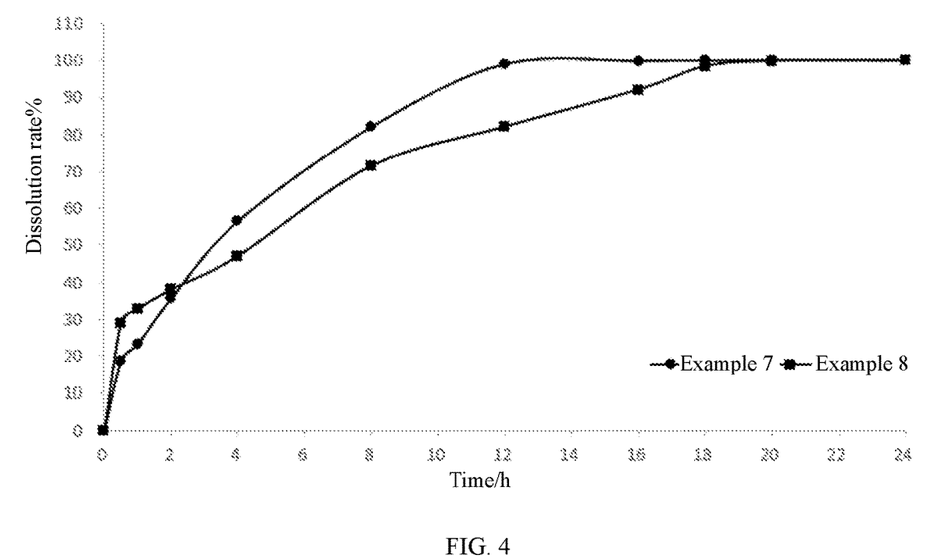
FIG. 4 shows in-vitro dissolution curves of the ibuprofen controlled-release tablets in examples 7-8.
Figure 7:
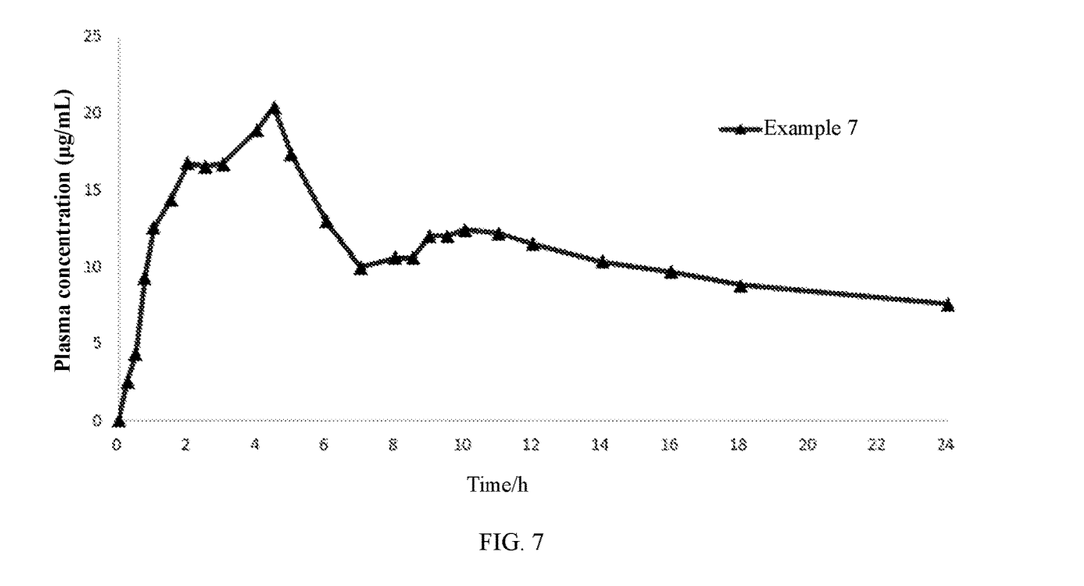
FIG. 7 shows an in-vivo curve of the ibuprofen controlled-release tablet in example 7.

A structure diagram of the tablet prepared by the method is shown in FIG. 2. In-vitro dissolution data of the tablets of example 7-8 and in-vivo data of the tablet of example 7 are shown in FIG. 4 and FIG. 7 respectively.

The present example verified in-vivo plasma concentrations of different formulations (example 2, example 3, and commercially available products). Basic information of the commercially available products is shown in the following table:

| Trade name | Factory | Batch No. | Specification remarks |
|---|---|---|---|
| Advil | Pfizer Consumer Healthcare, a division of Pfizer Canada Inc | L50926 | Immediate-release 200 mg |
| Advil ®12 Hour | Pfizer Consumer Healthcare, a division of Pfizer Canada Inc | W61840 | Immediate-release 200 mg + Sustained-release 400 mg |
| Brufen ®Retard | Mylan Products Ltd. | 85068PC | Sustained-release 800 mg |
| IBU ™ | Dr. Reddy's Laboratories LA LLC. | L700164 | Immediate-release 800 mg |

At present, ibuprofen on the market is divided into two types, an immediate-release type (Advil, IBU™) and a sustained-release type (Brufen® Retard). The immediate-release dosage releases rapidly. But since the ibuprofen has a short half-life period ($t_{1/2}$ about 2 h), the drug is quickly eliminated in the body, such that the drug efficacy cannot be sustained and a patient needs to be administered many times. At present, the sustained-release dosage on the market can take effect continuously for a certain period of time, reduce the number of times of administration, and improve compliance of a patient, but the drug cannot take effect quickly after the administration and cannot rapidly reduce pain of the patient. An only immediate-release and sustained-release preparation (Advil® 12 Hour) on the current market can take effect quickly after the administration, but cannot be continuously effective for 24 h. and still needs to be administered 2 times a day.

Figure 8:
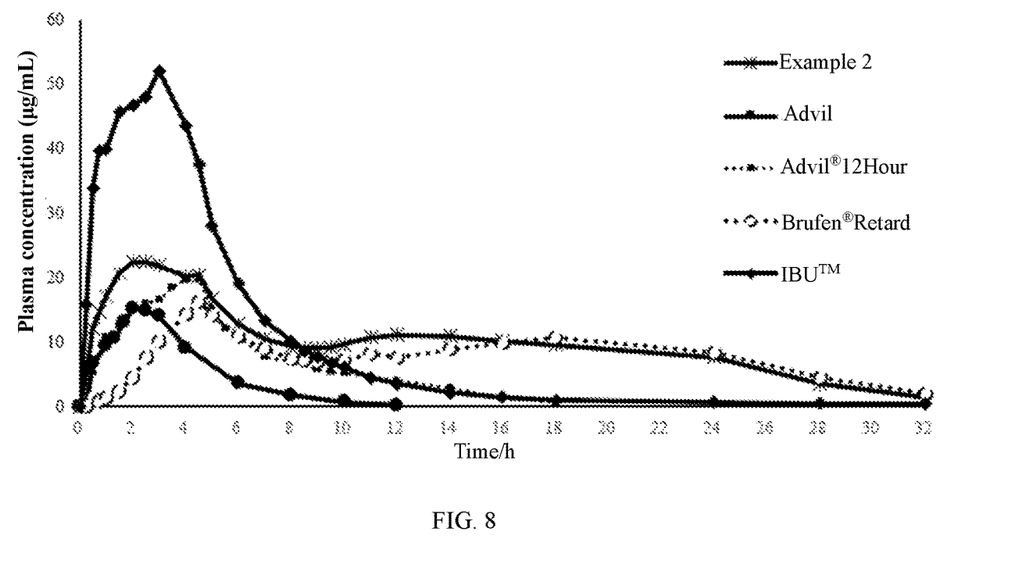
FIG. 8 shows in-vitro plasma concentration curves of example 2 and commercially-available ibuprofen products.

Test results are shown in FIG. 8. It can be seen that the plasma concentration of the tablet of example 2 within 0-4 h was higher than that commercially available preparations of Advil, Advil® 12 Hour, and Brufen® Retard, and the tablet of example 2 can take effect quickly. The plasma concentration of the tablet of example 2 within 12-24 h is all higher than that of 800 mg of an immediate-release tablet IBU™ and effective time is prolonged from 12 h to 24 h.

Example 10

Figure 9:
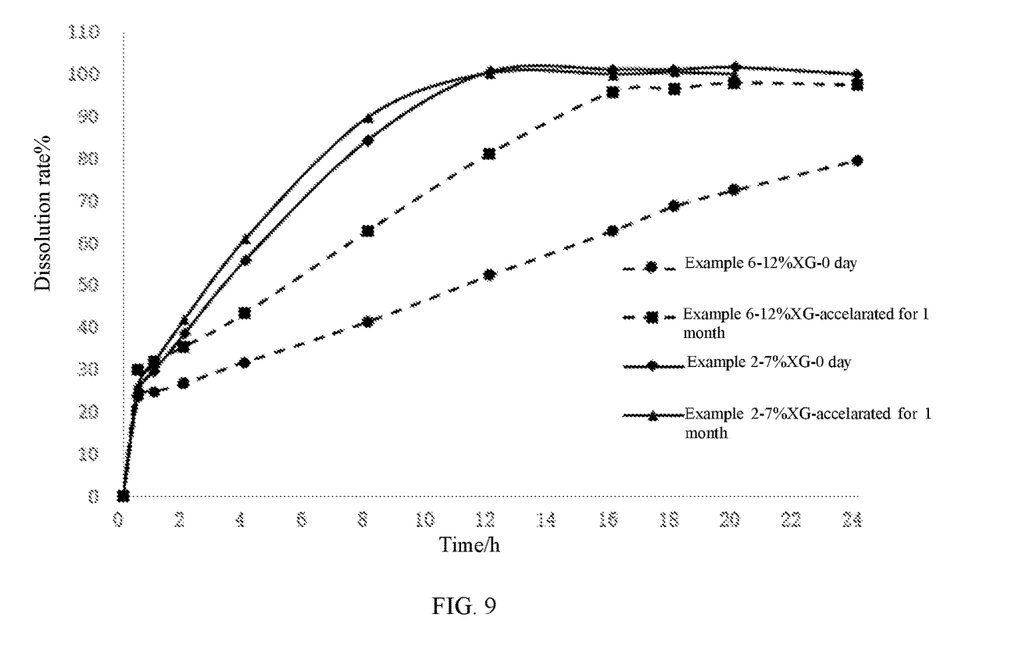
FIG. 9 shows comparison of stable dissolution of formulations with different xanthan gum proportions.

The present example verified a stable dissolution of formulations with different xanthan gum proportions (examples 2 and 6). The results are shown in FIG. 9. It can be seen that when the proportion of the xanthan gum in the formulation is greater than 10%, a dissolution rate in vitro will increase significantly after an accelerated stability test of the tablet for a period of time.

Hardness and fragility of the controlled-release tablets with different xanthan gum proportions (examples 2, 4, and 5) were detected. The results are shown in the following table:

| Example | Xanthan gum proportion | Hardness N | Fragility % | Cracked or not |
|---|---|---|---|---|
| Example 2 | 7% | 150-230 | 0.02 | No |
| Example 4 | 10% | 120-170 | 0.09 | No |
| Example 5 | 11% | 70-100 | 0.12 | Yes |

It can be seen that when the proportion of the xanthan gum in the formulation was greater than 10%, the hardness is low and the fragility is non-conformity (the tablet is cracked).

In conclusion, when the proportion of the xanthan gum in the formulation was greater than 10%, a plasma concentration cannot reach an analgesic effect (fasting plasma drug test data in example 5) and the formulation was not suitable for mass production.

Example 11

The present example verified effects of formulations I and II of a combination of an immediate-release layer and a sustained-release layer. Specific compositions of the formulations I and II are as follows:

| Tablet layer/proportion | Specification/tablet weight/formulation | Formulation I | Formulation II |
|---|---|---|---|
| Immediate-release layer | Specification | 200 mg | 200 mg |
| | Tablet weight | 400 mg | 400 mg |
| | Ibuprofen | 20.00% | 20.00% |
| | Filler (microcrystalline cellulose) | 14.40% | 14.40% |
| | Disintegrating agent (cross-linked sodium carboxymethyl cellulose) | 2.00% | 2.00% |
| | Adhesive (polyvinyl pyrrolidone K30) | 3.00% | 3.00% |
| | Flow aid (colloidal silicon dioxide) | 0.20% | 0.40% |
| | Lubricant (magnesium stearate) | 0.40% | 0.20% |
| Sustained-release layer | Specification | 400 mg | 400 mg |
| | Tablet weight | 600 mg | 600 mg |
| | Ibuprofen | 40.00% | 40.00% |
| | Sustained-release polymer (HPMC-K100LV) | 12.00% | / |
| | Sustained-release polymer (HPMC-K100M) | / | 18.00 |
| | Filler (microcrystalline cellulose) | 6.00% | / |
| | Flow aid (colloidal silicon dioxide) | 1.40% | 1.40% |
| | Lubricant (magnesium stearate) | 0.60% | 0.60% |

Figure 5:
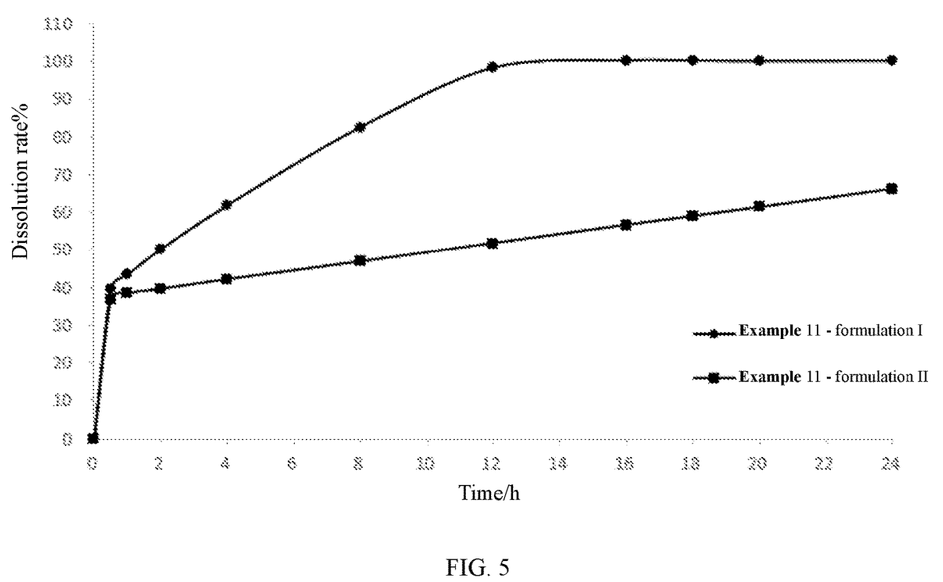
FIG. 5 shows in-vitro dissolution curves of formulations I and II.

In the formulation I, the sustained-release polymer is HPMC-K100LV with a content of 12% and a ratio of ibuprofen in a sustained-release layer to that in an immediate-release layer is 2. An in-vitro dissolution test was performed. Results are shown in FIG. 5. It can be seen that the drug in the sustained-release layer of the formulation I was completely released within 12 h and thus a long-acting analgesic effect within 24 h cannot be realized.

In the formulation II, the sustained-release polymer is HPMC-K100M with a content of 18% and a ratio of the ibuprofen in the sustained-release layer to that in an immediate-release layer is 2. An in-vitro dissolution test was performed. Results are shown in FIG. 5. It can be seen that although the formulation II continuously released for 24 h, but a release dissolution rate was only 66%. The release was incomplete, an ideal plasma concentration cannot be realized, namely the long-acting analgesic effect cannot be realized.

What is claimed is:

1. An ibuprofen controlled-release tablet, wherein the controlled-release tablet is composed of
a drug-containing immediate-release layer and a drug-containing sustained-release layer, a ratio of the mass of the ibuprofen in the drug-containing sustained-release layer to the mass of the ibuprofen in the drug-containing immediate-release layer falls into a range of 2.2:1-7:1;
wherein a sustained-release polymer in the drug-containing sustained-release layer is a combination of hydroxypropyl methylcellulose and xanthan gum, wherein
the xanthan gum in the sustained-release polymer constitutes 5-10 wt. % of the ibuprofen controlled-release tablet, and
the hydroxypropyl methylcellulose in the sustained-release polymer constitutes 1-25 wt. % of the ibuprofen controlled-release tablet and wherein a hardness of the ibuprofen controlled-release tablet is 120-230 N.

2. The ibuprofen controlled-release tablet according to claim 1, wherein the ratio of the mass of the ibuprofen in the drug-containing sustained-release layer to the mass of the ibuprofen in the drug-containing immediate-release layer falls into the range selected from 3:1-7:1, 4:1-7:1, 2.5-7:1, 6:1-7:1, 2.2:1-3:1, 2.2:1-4:1, 2.2:1-5:1, 2.2:1-6:1, 3:1-4:1, 4:1-5:1, and 5:1-6:1.

3. The ibuprofen controlled-release tablet according to claim 1, wherein the drug-containing immediate-release layer is composed of the following components: ibuprofen, a filler, an adhesive, a disintegrating agent, a lubricant, and a flow aid.

4. The ibuprofen controlled-release tablet according to claim 1, wherein calculated by the ibuprofen controlled-release tablet, the drug-containing immediate-release layer comprises 5.00-30.00 wt. % of the ibuprofen and 0.50-5.00 wt. % of a disintegrating agent.

5. The ibuprofen controlled-release tablet according to according to claim 1, wherein calculated by the ibuprofen controlled-release tablet, the drug-containing sustained-release layer comprises 30.00-65.00 wt. % of the ibuprofen and 5.00-25.00 wt. % of the sustained-release polymer.

6. The ibuprofen controlled-release tablet according to claim 1, wherein a mass ratio of the drug-containing sustained-release layer to the drug-containing immediate-release layer is 5.6:1 to 1.66:1.

7. The ibuprofen controlled-release tablet according to claim 1, wherein the ibuprofen controlled-release tablet is oval or capsule-shaped; and the drug-containing immediate-release layer and the drug-containing sustained-release layer separately constitute an upper layer and a lower layer of the ibuprofen controlled-release tablet.

8. The ibuprofen controlled-release tablet according to claim 1, wherein the ibuprofen controlled-release tablet further comprises a tablet core layer wrapped between the drug-containing immediate-release layer and the drug-containing sustained-release layer; and the tablet core layer is an immediate-release tablet core layer or a sustained-release tablet core layer.

9. The ibuprofen controlled-release tablet according to claim 8, wherein when the tablet core layer is the sustained-release tablet core layer, the tablet core layer is composed of the following components: the ibuprofen, a sustained-release polymer, a filler, a lubricant, a flow aid, and an enteric coating premix;
and when the tablet core layer is the immediate-release tablet core layer, the tablet core layer is composed of the following components: the ibuprofen, the filler, an adhesive, a disintegrating agent, the lubricant, the flow aid, and the enteric coating premix.

10. The ibuprofen controlled-release tablet according to claim 9, wherein when the tablet core layer is the sustained-release tablet core layer, a ratio of a sum of the mass of the ibuprofen in the drug-containing sustained-release layer and a mass of the ibuprofen in the sustained-release tablet core layer to the mass of the ibuprofen in the drug-containing immediate-release layer is 2.2:1 to 7:1, 3:1 to 7:1, 4:1 to 7:1, 2.5 to 7:1, 6:1 to 7:1, 2.2:1 to 3:1, 2.2:1 to 4:1, 2.2:1 to 5:1, 2.2:1 to 6:1, 3:1 to 4:1, 4:1 to 5:1, or 5:1 to 6:1, and a ratio of the mass of the ibuprofen in the drug-containing sustained-release layer to the mass of the ibuprofen in the sustained-release tablet core layer is 27:1 to 3:1 or 19:1 to 4.6:1;

when the tablet core layer is the immediate-release tablet core layer, a ratio of the mass of the ibuprofen in the drug-containing sustained-release layer to a sum of a mass of the ibuprofen in the immediate-release tablet core layer and the mass of the ibuprofen in the drug-containing immediate-release layer is 2.2:1 to 7:1, 3:1 to 7:1, 4:1 to 7:1, 2.5 to 7:1, 6:1 to 7:1, 2.2:1 to 3:1, 2.2:1 to 4:1, 2.2:1 to 5:1, 2.2:1 to 6:1, 3:1 to 4:1, 4:1 to 5:1, or 5:1 to 6:1, and a ratio of the mass of the ibuprofen in the drug-containing immediate-release layer to the mass of the ibuprofen in the immediate-release tablet core layer is 11:1 to 1:1 or 10:1 to 2:1.

11. The ibuprofen controlled-release tablet according to claim 8, wherein a filler in the drug-containing immediate-release layer, the drug-containing sustained-release layer, the immediate-release tablet core layer, and the sustained-release tablet core layer is independently selected from one or more of lactose, corn starch, pregelatinized starch, and microcrystalline cellulose.

12. The ibuprofen controlled-release tablet according to claim 8, wherein an adhesive in the drug-containing immediate-release layer and the immediate-release tablet core layer is independently selected from one or more of sodium carboxymethyl cellulose, polyvinyl pyrrolidone, hydroxypropyl methylcellulose (HPMC), and hydroxypropyl cellulose (HPC).

13. The ibuprofen controlled-release tablet according to claim 8, wherein a disintegrating agent in the drug-containing immediate-release layer and the immediate-release tablet core layer is independently selected from one or more of cross-linked sodium carboxymethyl starch, cross-linked sodium carboxymethyl cellulose, cross-linked polyvinyl pyrrolidone (PVPP), and low-substituted hydroxypropyl cellulose (L-HPC).

14. The ibuprofen controlled-release tablet according to claim 8, wherein a lubricant in the drug-containing immediate-release layer, the drug-containing sustained-release layer, the immediate-release tablet core layer, and the sustained-release tablet core layer is independently selected from one or more of magnesium stearate, stearic acid, sodium stearyl fumarate, glyceryl behenate, hydrogenated castor oil, and sodium dodecyl sulfate.

15. The ibuprofen controlled-release tablet according to claim 8, wherein a flow aid in the drug-containing immediate-release layer, the drug-containing sustained-release layer, the immediate-release tablet core layer, and the sustained-release tablet core layer is independently selected from colloidal silicon dioxide and talc powder.

16. The ibuprofen controlled-release tablet according to claim 8, wherein a sustained-release polymer in the sustained-release tablet core layer is a combination of hydroxypropyl methylcellulose and xanthan gum.

17. The ibuprofen controlled-release tablet according to claim 8, wherein an enteric coating premix in the immediate-release tablet core layer and the sustained-release tablet core layer is independently selected from one or more of a methacrylic acid copolymer, and polyvinyl acetate phthalate.

18. The ibuprofen controlled-release tablet according to claim 1, wherein the hydroxypropyl methylcellulose in the sustained-release polymer is 1.58-16.9 wt. % in the ibuprofen controlled-release tablet.

19. The ibuprofen controlled-release tablet according to claim 16, wherein the hydroxypropyl methylcellulose in the sustained-release polymer has a viscosity range of 3-2,000 mpa·s.

20. A method for preparing the ibuprofen controlled-release tablet according to claim 1, comprising the following steps:
a. weighing a formulation amount of the ibuprofen and a filler required to prepare the drug-containing immediate-release layer, performing a first wet granulation by using first purified water or a first alcohol solution, passing a first wet particle through a first 1,000-8,000 μm sieve, drying the first wet particle, passing a first dried particle through the first 1,000-8,000 μm sieve, adding an adhesive, a disintegrating agent, and a flow aid to a first sieved particle to obtain a first mixture, pre-mixing the first mixture, and then adding a lubricant to be mixed to prepare a drug-containing immediate-release layer particle for later use;
b. weighing a formulation amount of the ibuprofen, a sustained-release polymer, and the filler required to prepare the drug-containing sustained-release layer, performing a second wet granulation by using second purified water or a second alcohol solution, passing a second wet particle through a second 1,000-8,000 μm sieve, drying the second wet particle, passing a second dried particle through the second 1,000-8,000 μm sieve, adding the flow aid to a second sieved particle to obtain a second mixture, pre-mixing the second mixture, and then adding the lubricant to be mixed to prepare a drug-containing sustained-release layer particle for later use; and
c. placing a formulation amount of the drug-containing sustained-release layer particle into a punching die of a tablet machine for pre-pressing; and then placing a formulation amount of the drug-containing immediate-release layer particle into the punching die to be pressed into the ibuprofen controlled-release tablet.

21. The method according to claim 20, wherein in step c, a pre-pressure is 0.1-2 KN or 0.1-0.5 KN; and a main pressure is 5-60 KN or 10-50 KN.

22. A method for preparing the ibuprofen controlled-release tablet according to claim 8, comprising the following steps:
a. weighing a formulation amount of the ibuprofen and a filler required to prepare the drug-containing immediate-release layer, performing a first wet granulation by using first purified water or a first alcohol solution, passing a first wet particle through a first 1,000-8,000 μm sieve, drying the first wet particle, passing a first dried particle through the first 1,000-8,000 μm sieve, adding an adhesive, a disintegrating agent, and a flow aid to a first sieved particle to obtain a first mixture, pre-mixing the first mixture, and then adding a lubricant to be mixed to prepare a drug-containing immediate-release layer particle for later use;
b. weighing a formulation amount of the ibuprofen, a sustained-release polymer, and the filler required to prepare the drug-containing sustained-release layer, performing a second wet granulation by using second purified water or a second alcohol solution, passing a second wet particle through a second 1,000-8,000 μm sieve, drying the second wet particle, passing a second dried particle through the second 1,000-8,000 μm sieve, adding the flow aid to a second sieved particle to obtain a second mixture, pre-mixing the second mixture, and then adding the lubricant to be mixed to prepare a drug-containing sustained-release layer particle for later use;

c. placing a part of the drug-containing immediate-release layer particle prepared in step a or a part of the drug-containing sustained-release layer particle prepared in step b into a punching die of a tablet machine to be pressed into a plain tablet core;

e. weighing a formulation amount of an enteric coating premix and preparing the enteric coating premix into an enteric coating solution by using a third alcohol solution; and placing the plain tablet core pressed in step c in a coating machine and performing a coating by using the enteric coating solution to prepare a tablet core layer for later use; and f. placing a formulation amount of the drug-containing sustained-release layer particle into the punching die of the tablet machine, placing the tablet core layer on the drug-containing sustained-release layer particle for pre-pressing; and then placing a formulation amount of the drug-containing immediate-release layer particle into the punching die to be pressed into the ibuprofen controlled-release tablet.

23. The method according to claim 22, wherein in step f, a pre-pressure is 0.1-2 KN or 0.1-0.5 KN; and a main pressure is 5-60 KN or 10-50 KN.

24. A method for preparing the ibuprofen controlled-release tablet according to claim 1, comprising the following steps:

a. weighing a formulation amount of the ibuprofen and a filler required to prepare the drug-containing immediate-release layer, performing a first wet granulation by using first purified water or a first alcohol solution, passing a first wet particle through a first 1,000-8,000 μm sieve, drying the first wet particle, passing a first dried particle through the first 1,000-8,000 μm sieve, adding an adhesive, a disintegrating agent, and a flow aid to a first sieved particle to obtain a first mixture, pre-mixing the first mixture, and then adding a lubricant to be mixed to prepare a drug-containing immediate-release layer particle for later use;

b. weighing a formulation amount of the ibuprofen, a sustained-release polymer, and the filler required to prepare the drug-containing sustained-release layer, performing a second wet granulation by using second purified water or a second alcohol solution, passing a second wet particle through a second 1,000-8,000 μm sieve, drying the second wet particle, passing a second dried particle through the second 1,000-8,000 μm sieve, adding the flow aid to a second sieved particle to obtain a second mixture, pre-mixing the second mixture, and then adding the lubricant to be mixed to prepare a drug-containing sustained-release layer particle for later use;

c. placing a part of the drug-containing immediate-release layer particle prepared in step a or a part of the drug-containing sustained-release layer particle prepared in step b into a punching die of a tablet machine to be pressed into a plain tablet core;

e. weighing a formulation amount of an enteric coating premix and preparing the enteric coating premix into an enteric coating solution by using a third alcohol solution; and placing the plain tablet core pressed in step c in a coating machine and performing a coating by using the enteric coating solution to prepare a tablet core layer for later use; and f. placing a formulation amount of the drug-containing sustained-release layer particle into the punching die of the tablet machine, placing the tablet core layer on the drug-containing sustained-release layer particle for pre-pressing; and then placing a formulation amount of the drug-containing immediate-release layer particle into the punching die to be pressed into the ibuprofen controlled-release tablet.

25. The method according to claim 24, wherein in step f, a pre-pressure is 0.1-2 KN or 0.1-0.5 KN; and a main pressure is 5-60 KN or 10-50 KN.

26. The ibuprofen controlled-release tablet according to claim 1, wherein an in vitro dissolution rate is 20%-40% for 1 h and >90% for 18 h in 900 mL dissolution medium of a phosphate buffer solution at a pH of 7.2+2% SDS, under conditions of a rotation speed of 200 rpm, and a solution temperature of 37° C.

* * * * *